United States Patent [19]

Lazzeri et al.

[11] Patent Number: 4,963,155
[45] Date of Patent: Oct. 16, 1990

[54] ATTACHMENT MECHANISM FOR MODULAR SURGICAL PRODUCTS

[75] Inventors: Mark A. Lazzeri; Roy Y. Hori; James C. Harris, all of Warsaw, Ind.

[73] Assignee: Zimmer, Inc., Warsaw, Ind.

[21] Appl. No.: 400,633

[22] Filed: Aug. 30, 1989

[51] Int. Cl.$^5$ .............................. A61F 2/32; A61F 5/04
[52] U.S. Cl. ........................................ 623/23; 623/16; 606/85; 606/86
[58] Field of Search .................... 623/16, 18, 19, 20, 623/21, 22, 23; 606/60, 62, 65, 67, 69, 71, 72, 86, 85, 87, 88, 89, 90, 91, 96, 99

[56] References Cited

U.S. PATENT DOCUMENTS

| | | | |
|---|---|---|---|
| 4,676,797 | 6/1987 | Anapliotis et al. | 623/18 |
| 4,834,758 | 5/1989 | Lane et al. | 623/18 |
| 4,857,964 | 8/1989 | Walker et al. | 128/92 |

FOREIGN PATENT DOCUMENTS

0257359 A1  3/1988  European Pat. Off. .

OTHER PUBLICATIONS

Zimmer catalog pp. A 22, 28, 33, 35, 42, 43—Various rasp and cone provisional products—1987.

Primary Examiner—David J. Isabella
Attorney, Agent, or Firm—Margaret L. Geringer

[57] ABSTRACT

A set of surgical products which includes an attachment mechanism for modular surgical products. The set includes a plurality of first components and a plurality of second components. One of the first components and one of the second components are to be selected for engagement with each other. The components each include an indexing means including a key on the first components and a corresponding slot on the second components for mating with the key. The orientations of the keys and slots vary, so that only first components having a key orientation that is similar to and aligns with the slot orientation of a second component will properly mate together and so that first components will not properly align and mate with second components having slot orientations that are different from the respective key orientation.

18 Claims, 2 Drawing Sheets

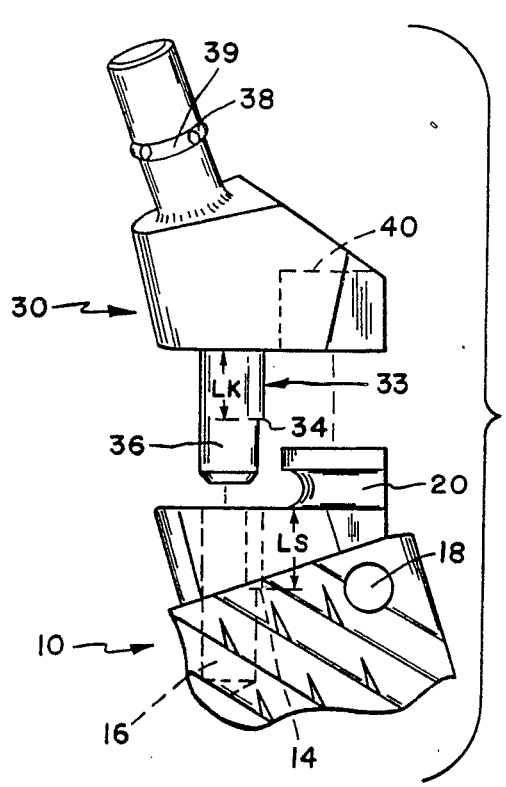
FIG. 1
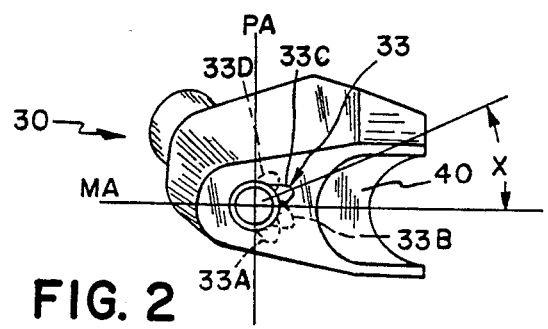
FIG. 2
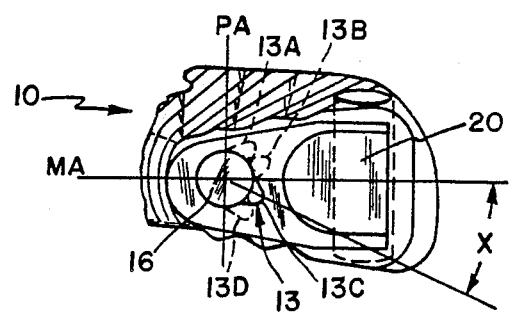
FIG. 3
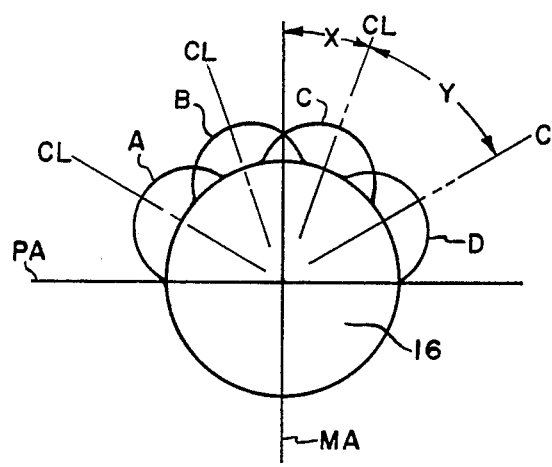
FIG. 6
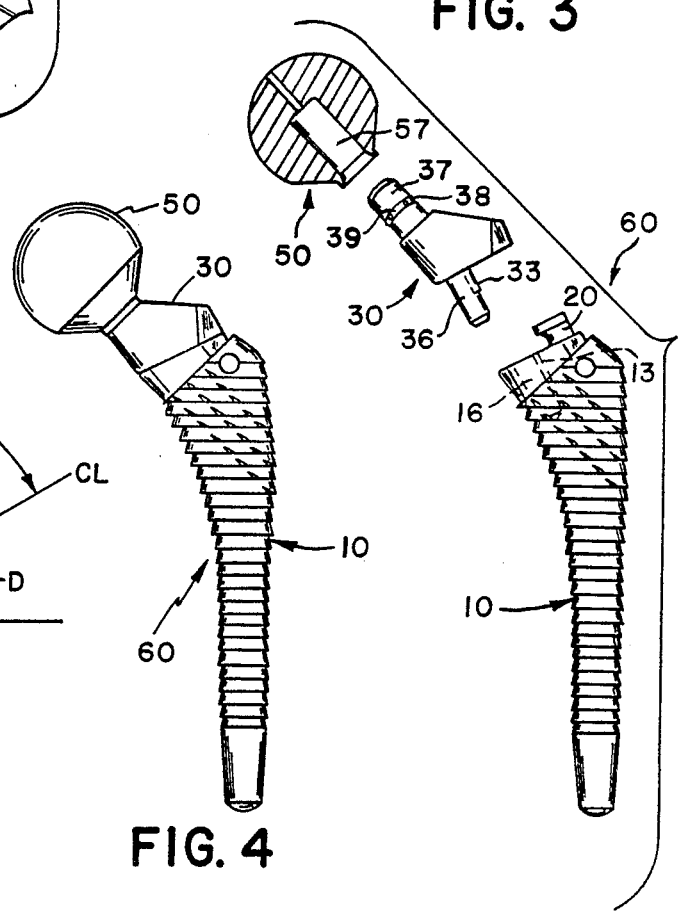
FIG. 4
FIG. 5

ATTACHMENT MECHANISM FOR MODULAR SURGICAL PRODUCTS

The present invention relates to an attachment mechanism for modular surgical products. The attachment mechanism includes an indexing means to selectively orient certain sizes of first components for attachment to certain sizes of second components and to help prevent the wrong size first component from being utilized with the wrong size second component.

European Patent EP No. 0 257 359 A1 to Bolesky et al. discloses a modular hip prosthesis in which a body member 55 includes a key 58 that is received in a keyway 60 that is formed in the stem 20. The key 58 and keyway 60 cooperate to prevent any rotation of the body member 55 with respect to the stem member 20. This patent illustrates in FIG. 2 the key and keyway on the lateral side of the implant and also illustrates in FIG. 4 an alternate embodiment that the key and keyway could be located on the medial side of the implant. However, all of the implants in each respective embodiment have the key and keyway aligned in one orientation within the kit or set of modular components to enable any selected body member 55 to fit with any selected stem 20.

U.S. Pat. No. 4,834,758 to Lane et al. discloses a lug 258 which projects from the neck and serves as a key by reception in notch 516 of the component 500 for maintaining rotational integrity in the coupling. (See FIGS. 35, 36, 37, 42, 43, 44, 47.) In addition, FIGS. 57, 59, and 64 show a lug 618 for rotational keying. The two spaced apart notches 620, the appropriate one of which receives a finger 556 of collar 550 are shown in FIG. 50. The location of the lug 618 is established to orient the neck of the component 600 to the femur. Component 600 can be made in right and left versions by relocating the lug 618 in mirror-image positions. The shaft component 500 can be standardized then for all uses in the thigh and leg.

In addition, U.S. Pat. No. 4,587,964 to Walker et al. discloses a rasp tool with a removable handle. After the rasp has been used to rasp/cut the bone, such as in the femoral canal, the removable handle may be removed and the rasp left in the canal. An appropriate sized cone provisional, such as those sold by Zimmer, Inc., may be added to the corresponding size rasp. An appropriate sized femoral ball head is added to the cone provisional to complete the trial prosthesis for a femoral component which is used for trial reduction and range of motion analysis during surgery. A typical connection between the rasp and cone provisional includes a first protruding cylindrical peg on the rasp to fit in a corresponding hole in the cone provisional and a second protruding cylindrical peg on the cone provisional to fit in a corresponding hole in the rasp. This dual peg-in-hole connection prevents rotation of the cone provisional with respect to the rasp. Typically, any size of cone provisional could fit on any size of rasp.

OBJECTS OF THE INVENTION

It is an object of the present invention to provide a set of surgical products which includes a plurality of first and second components in which only select first components are attachable to select second components.

It is a further object of the invention to provide an indexing means to allow only certain components within a set to be properly attached together.

SUMMARY OF THE INVENTION

The present invention provides a set of surgical products which includes an attachment mechanism for modular surgical products. The set includes a plurality of first components and a plurality of second components. One of the first components and one of the second components are to be selected for engagement with each other. The components each include an indexing means including a key on the first components and a corresponding slot on the second components for mating with the key. The orientations of the keys and slots vary, so that only first components having a key orientation that is similar to and aligns with the slot orientation of a second component will properly mate together, and so that first components will not properly align and mate with second components having slot orientations that are different from the respective key orientation.

BRIEF DESCRIPTION OF THE DRAWINGS

These features and objects of the invention, as well as others, will become apparent to the skilled in the art by referring to the accompanying drawings:

FIG. 1 is an exploded perspective view of a cone provisional and a partial perspective view of a rasp in accordance with the present invention;

FIG. 2 is a bottom view of the cone provisional of FIG. 1;

FIG. 3 is a top view of the rasp of FIG. 1;

FIG. 4 is an assembled side view of the rasp and cone provisional of FIG. 1, shown with a provisional head assembled to the cone provisional;

FIG. 5 is an exploded side view of the components shown in FIG. 4;

FIG. 6 is a schematic representation of the relative orientations of the slots in a set of surgical products for a particularly advantageous embodiment of the present invention;

DETAILED DESCRIPTION OF THE INVENTION

Figure 7:
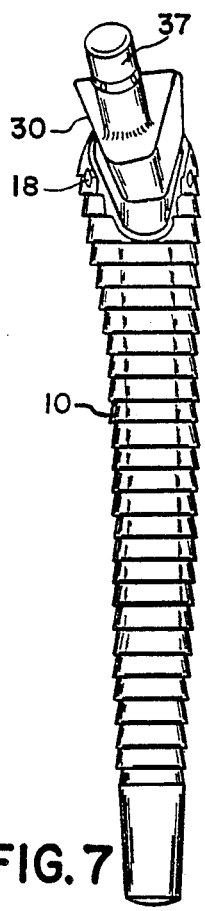
FIG. 7 is a front view of a size 12 right rasp assembled with a size 12-13 right cone provisional.

FIGS. 1-5 illustrate a particularly advantageous embodiment of an attachment mechanism for a set of modular surgical products. The set includes a plurality of first components 30 and a plurality of second components 10. The invention will be described with reference to a particularly advantageous set of modular surgical products where the first components 30 are cone or neck provisionals which are adapted to attach to second components 10 which are rasp stems. However, it is understood that this attachment mechanism of the present invention may be utilized with other types of first and second components where it is desirable to provide an indexing means to allow only certain components within a set to be properly attached together.

With reference to the FIGS. 1-5, although only a single first component (cone provisional) 30 is shown with only a single second component (rasp item) 10, it is understood that multiple cone provisionals 30 and multiple rasp stems 10 could be provided. The cone provisional 30 and rasp stems 10 may be provided in multiple sizes, with varying features such as different lengths, different widths, different angles, etc. One of the cone provisionals 30 is selected to fit with one of the corresponding rasp stems 10. An appropriate size provisional head 50 is then selected to attach to the cone provisional 30 to form a trial hip prostheses 60. It is typical to utilize a trial prostheses to evaluate fit before implanting the actual hip stem prosthesis implant.

The first and second components 30 and 10 of the present invention each include an indexing means which is comprised of a protrusion or rib or key 33 on the first components 30 and a corresponding indentation or slot 13 on the second component 10 for mating with the key 33. The orientations of the keys 33 and slots 13 vary, so that only first components 30 having a key orientation that is similar to and properly aligns with the slot orientation of a second component 10 will properly mate together, and so that first components 30 will not be properly aligned and thus will not properly mate with second components 10 having slot 13 orientations that are different from the respective key 33 orientation of the first component 30.

In a particularly advantageous embodiment, the set of surgical products includes a plurality of first components 30 and a plurality of second components 10 where one of the first components 30 and one of the second components 10 are selected for engagement with each other. The first components 30 each have a male peg 36 extending therefrom with a key 33 protruding from each respective peg 36. The second components 10 each have a female recess 16 with a slot 13 in each respective recess 16 for corresponding engagement with one of the keyed pegs 36. The plurality of first components 30 includes a first group of one or more first components 30 in which the key 33 is at a first orientation "A" (thus key 33A) with respect to the peg 36 and a second group of one or more first components 30 in which the key 33 is at a second orientation "B" (thus key 33B) different from the first orientation "A" with respect to the peg 36. In addition, the plurality of second components 10 includes a first group of one or more second components 10 in which the slot 13 is at a first orientation "A" (thus slot 13A) with respect to the recess 16, and a second group of one or more second components 10 in which the slot 13 is at a second orientation "B" (thus slot 13B) different from the first orientation "A" with respect to the recess 16. The first key orientation 33A is aligned with and corresponds to the first slot orientation 13A and the second key orientation 33B is aligned with and corresponds to the second slot orientation 13B, such that the first group of first components is adapted to properly align with and attach to only the first group of second components, while the second group of first components is adapted to properly align with and attach to only the second group of second components.

A third and a fourth (and even more, if desired) group of one or more first components and third and a fourth (and even more, if desired) group of one or more second components may also be provided. The third group having third key and slot orientations 33C and 13C, respectively, and the fourth group having fourth key and slot orientations of 33D and 13D, respectively. The third and fourth orientations "C" and "D" are different from each other and different from the first and second orientations "A" and "B". The first components 30 having the third key orientation 33C correspond with the second components 10 having the third slot orientation 13C, while the first components 30 having the fourth orientation 33D correspond with the second components 10 having the fourth slot orientation 13D. Thus, the third group of first components is adapted to properly align with and attach to only the third group of second components, while the fourth group of first components is adapted to properly align with and attach to only the fourth group of second components, and so on.

FIG. 2 illustrates a cone provisional 30 having a key 33 at the "C" orientation (key 33C). Keys at an "A", "B", and "D" orientation (keys 33A, 33B, and 33D) are represented by the indicated phantom lines to show their relative orientation to the peg 36 and to each other. FIG. 3 illustrates a top portion of a rasp stem 10 having a corresponding slot 13 at the "C" orientation (slot 13C). Slots at "A", "B", and "D" orientations (slots 13A, 13B, and 13D) are represented by the indicated phantom lines to show their relative orientation to the recess 16 and to each other. Since FIG. 2 is a bottom view looking up at the peg 36 and FIG. 3 is a top view looking down at the recess 16, the arrangement of orientations "A", "B", "C", and "D" appear to be mirror images of each other. However, it can be seen that when the cone provisional 30 is positioned over the rasp stem 10, as in FIG. 1, the key 33C would line up directly with and thus correspond with slot 13C.

FIG. 6 is an enlarged schematic representation of the relative orientations of positions "A", "B", "C", and "D" for the slots 13 shown looking into and relative to recess 16 and corresponding to the positions shown in FIG. 3. The corresponding relative orientations of positions "A", "B", "C", and "D" for the keys 33 can be seen from FIG. 2. The shape of the peg 36 and corresponding recess 16 ma appropriately be substantially cylindrical as shown in FIGS. 1-6. The peg 36 and recess 16 are shown as having a main axis "MA" and a secondary axis "PA" which is perpendicular thereto. Orientations "A", "B", "C", and "D" are angularly offset from each other. The centerlines "CL" of each adjacent orientation ar 40° apart (angle Y) from each other, while the centerlines of the orientations adjacent the main axis "MA" are 20°. (angle X) from the main axis "MA". The angles between the different positional orientations may vary as desired and as appropriate.

Figure 11:
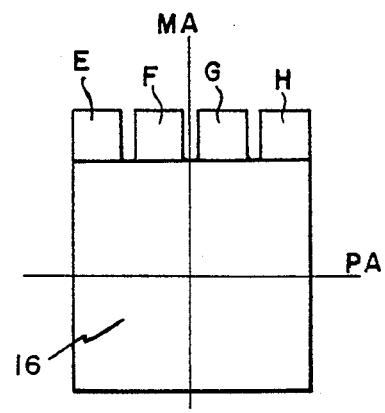
FIG. 11 is a schematic representation of an alternate embodiment for the relative orientations of the slots in a set of surgical products.
Figure 12:
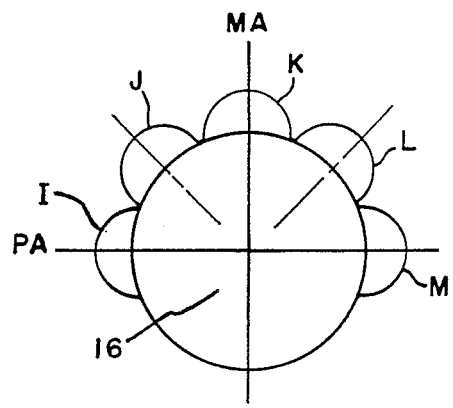
FIG. 12 is a schematic representation of a further alternate embodiment for the relative orientations of the slots in a set of surgical products.

FIGS. 11 and 12 show two different alternate orientation arrangements. FIG. 11 illustrates orientations "E", "F", "G", and "H" for the relative orientations for slots 13 in which the cross-sectional shape of recess 16 is substantially rectangular. The corresponding peg 36 showing the relative orientations of keys 33 is not shown, but would have a substantially rectangular cross-section corresponding to the recess 16 shown in FIG. 11, with corresponding orientations "E", "F", "G", and "H" for keys 33. The orientations in FIG. 11 are offset in a linear fashion. FIG. 12 illustrates relative orientations "I", "J", "K", "L", and "M" for slots 13 with respect to recess 16. This FIG. 12 shows an angular variation for the orientations which could be used about a substantially cylindrical recess !6. The corresponding peg 36 showing the relative orientations of keys 33 is not shown, but would be substantially cylindrical to correspond with recess 16 shown in FIG. 12, with corresponding orientations "I", "J", "K", "L", and "M" for keys 33. The centerlines of orientations "I" and "M" are 90° from the main axis "MA" (which coincides with the centerline of "K", while the centerline for orientations "J" and "L" are 45° from the main axis "MA". It is noted that any suitably shaped recess/peg which can be adapted to indexing the components by varying slot/key orientation may be utilized.

An example of a representative set of surgical instrument components is described in the following "chart 1" which is based upon the key 33 and slot 13 orientations "A", "B", "C", and "D" from FIGS. 2, 3, and 6:

(not shown) for right components, so that a mixup of a left first component with a right second component (or vice versa) is very unlikely. Also, the largest (size 18) and smallest (size 10) also utilize like orientations (A). However, since the largest and smallest sizes are so visually different in their relative size, it is considered unlikely that the user would inadvertently and improperly attach one of the largest (size 18) components to one of the smallest (size 10) components. However, if one desired to eliminate this potential, the largest (size 18) and smallest (size 10) could also be made with different orientations.

In the set in instruments described in chart 1, it is also noted that one cone provisional 30 may be sized to fit two different size rasp stems 10. For example, a single cone provisional (size 12–13) is sized to fit two different

CHART 1:

| CONE PROVISIONAL 1ST COMPONENT(SIZE) | KEY ORIENTATION | SLOT ORIENTATION | RASP STEM 2ND COMPONENT(SIZE) |
|---|---|---|---|
| 1. 10–11 mm left* | A | A | 10 mm left+ |
| 2. 10–11 mm left* | A | A | 11 mm left+ |
| 3. 12–13 mm left*** | C | C | 12 mm left+++ |
| 4. 12–13 mm left*** | C | C | 13 mm left+++ |
| 5. 14–15 mm left** | B | B | 14 mm left++ |
| 6. 14–15 mm left** | B | B | 15 mm left++ |
| 7. 16–17 mm left**** | D | D | 16 mm left++++ |
| 8. 16–17 mm left**** | D | D | 17 mm left++++ |
| 9. 18 mm left* | A | A | 18 mm left+ |
| 10. 10–11 mm right* | A | A | 10 mm right+ |
| 11. 10–11 mm right* | A | A | 11 mm right+ |
| 12. 12–13 mm right*** | C | C | 12 mm right+++ |
| 13. 12–13 mm right*** | C | C | 13 mm right+++ |
| 14. 14–15 mm right** | B | B | 14 mm right++ |
| 15. 14–15 mm right** | B | B | 15 mm right++ |
| 16. 16–17 mm right**** | D | D | 16 mm right++++ |
| 17. 16–17 mm right**** | D | D | 17 mm right++++ |
| 18. 18 mm right* | A | A | 18 mm right+ |

*1st group of 1st components 30
**2nd group of 1st components 30
***3rd group of 1st components 30
****4th group of 1st components 30
+1st group of 2nd components 10
++2nd group of 2nd components 10
+++3rd group of 2nd components 10
++++4th group of 2nd components 10

A set of modular surgical products may include the above-identified series of first components 30 and second components 10. First components 30 which have a particular key orientation are adapted to attach to second components 10 having a like or corresponding slot orientation. However, it is noted that the intended cone provisional 30 is listed linearly across from the preferred mating rasp stem 10. As can be seen, all intended mating components have the same or like key/slot 33/13 orientation. "A" keys will only properly align with and thus properly fit into an "A" slot. Otherwise, the first component 30 will be visibly misaligned or disoriented (either angularly, if the orientations are angularly different, or linearly, if linearly offset, etc.) with respect to the second component 10. However, it is noted that a system may include left components and right components for a left hip or right hip, respectively (as in the present example of trial prostheses for a hip stem implant). While, it would not be desirable to improperly attach a left cone provisional 30 to a right rasp stem 10, or vice versa, it is not believed to be a problem in the present example to provide similar or like key/slot 33/13 orientations in the left set as in the right set because the left components preferably are arranged in a case (not shown) for left components and the right components preferably are arranged in a separate case rasp stems (a size 12 and a size 13). Thus, the size 12–13 cone provisional 30 with a "C" oriented key 33 may be utilized with a size 12 rasp stem 10 or a size 13 rasp stem 10 which both have "C" oriented slots 13.

Figure 8:
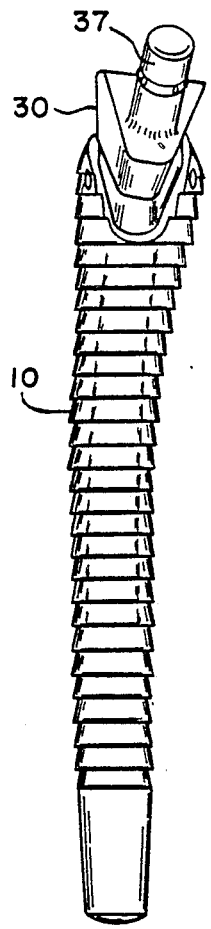
FIG. 8 is a front view of a size 13 left rasp assembled with a size 12-13 left cone provisional.

FIG. 7 illustrates a size 12 right rasp stem 10 properly attached to a size 12–13 right cone provisional 30. FIG. 8 illustrates a size 13 left rasp stem 10 properly attached to a size 12–13 left cone provisional 30.

Figure 9:
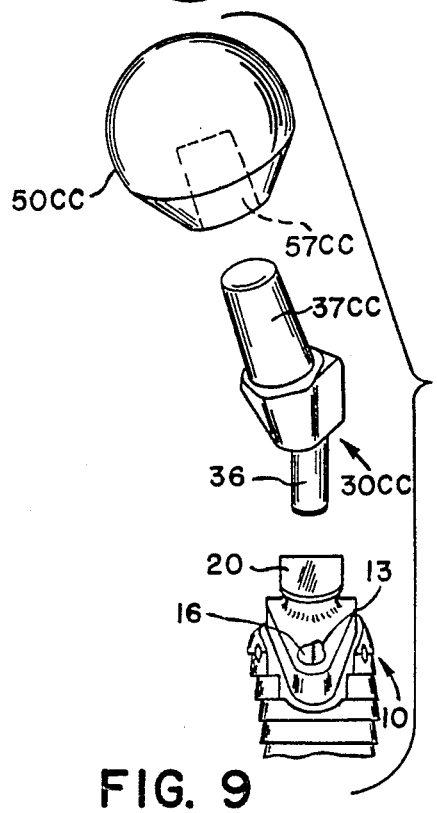
FIG. 9 is an exploded front perspective view of a rasp (partial), an alternate style cone provisional, and an alternate style provisional head.

It is noted that the cone provisionals 30 may include a second peg 37 for connection to the appropriate provisional head 50 as shown in FIG. 5. The second peg 37 is substantially cylindrical with a resilient C-shaped clip 38 in groove 39 in second peg 37 which aids in attaching head 50 via cylindrical recess 57 to second peg 37. Alternately, as shown in FIG. 9, the second peg 37 "CC" of cone provisional 30 "CC" may have a conical shape to attach to provisional head 37 "CC" with conical recess 57 "CC".

Each of the plurality of second components 10 includes a raised spline 20 spaced from the corresponding respective recess 16 as shown in FIGS. 1, 3, 5, and 9. Each of the plurality of first components 30 includes an opening 40 for fitting about the spline 20 when a cone provisional 30 is in mating engagement with a corresponding rasp stem 10 as shown in FIGS. 1, 2, 5, and 9.

The opening 40 may be U-shaped and thus open at the rear as shown in FIG. 2.

The combination of the interconnection of the spline 20 with the U-shaped opening 40 and the interconnection of the keyed peg 36 with the slotted recess 16 (which is spaced from the spline 20/opening 40) promotes rotational stability of the first and second components 30 and 10 when connected with each other. The length "LK" of the key 33 may suitably correspond with the length "LS" of the slot 13. The key length "LK" and slot length "LS" are designed so that if the neck or cone provisional 30 is placed on the incorrect rasp (one with a different key/slot orientation) the U-shaped opening 40 will not lock up with the spline 20. The slot 13 forms a ledge 14 which may seat with the ledge 34, on key 33 when a cone provisional 30 is properly interconnected to a corresponding rasp stem 10.

Figure 10:
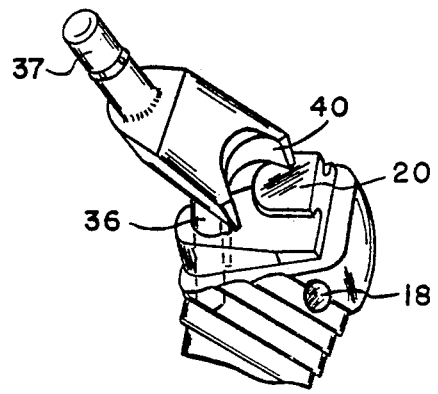
FIG. 10 is a perspective view of a mismatched rasp and cone provisional.

FIG. 10 illustrates a size 14–15 left cone provisional 30 (with a "B" orientation) improperly connected to a size 13 left rasp stem (with a "C" orientation). It is noted that when first component 30 with a key orientation that is different from a slot orientation of a second component 10 is attempted to be connected together, the parts will be visually out of line with each other due to the misalignment between the parts. However, with the additional raised spline 20, the misalignment also prevents the U-shaped opening 40 from fitting over the spline 20, and thus the first and second components with different key/slot orientations will not even seat properly together as shown in FIG. 10.

It is noted that the rasp stem 10 includes a transverse hole 18. An elongated rod may be inserted therethrough to assist in removal of the rasp stem 10 from the femoral canal. This is type of removal hole 18 is well known in the art.

It is further noted in referring to the present invention, that it is understood that while the invention has been described with the first component 30 having the protruding keyed peg 36 to fit in the corresponding slotted recess 16 of the second component 10, that the reverse arrangement (not shown) of the first component having the slotted recess and the second component having the corresponding keyed peg could also be utilized in keeping with the present invention. Further, it is also understood that rather than the peg 36 having protruding key 33 to fit in the recess 16 with slot 13, the reverse arrangement (not shown) of the peg 36 having a slot to fit in a corresponding recess 16 with a protruding key, could also be utilized in keeping with the present invention, and as such, would be considered substantially equivalent.

With regard to manufacturing the present invention, it is noted that any suitable manufacturing methods may be utilized. Further, any suitable materials may be utilized. One such appropriate material for the cone provisional 30 and rasp stems 10, which are described herein, is stainless steel, although any suitable material could be used.

The rasp stems 10 described herein may be utilized with a rasp handle (not shown) to rasp and size a femoral canal. The handle is then removed and the rasp stem 10 left in the femoral canal for use with the appropriate cone provisional 30 and provisional head 50 for use as a trial prosthesis. It is noted that the slots 13 in respective recesses 16 on each rasp stem 10 are located in positions where they encounter low impact loads during the rasping procedure with the rasp handle connected.

In summary, the relative orientations of the keys on first components and corresponding slots on second components vary, such that only first components having a like key orientation that is similar to and aligns with the slot orientation of a corresponding second component will properly align and mate together; and so that first components will not properly align and mate with second components having slot orientations that are different from the respective key orientation. This helps to ensure that the proper first components are used on the proper second components. The number of key/slot orientations and the selection of which first components are adapted to fit with which second components is left to the discretion and imagination of the person establishing the system or set. While this invention has been described and exemplified in terms of a particularly advantageous embodiment, those skilled in the art can appreciate that modifications can be made without departing from the spirit and scope of this invention.

What is claimed is:

1. A set of surgical products including a plurality of first components and a plurality of second components wherein one of the first components and one of the second components are selected for engagement with each other and wherein the first components each have a male peg extending therefrom with a key protruding from each respective peg and wherein the second components each have a female recess with a slot in each respective recess for corresponding engagement with one of the keyed pegs, and wherein the plurality of first components includes a first group of one or more first components in which the respective key is at a first orientation relative to the respective peg and a second group of one or more first components in which the respective key is at a second orientation different from the first orientation relative to the respective peg, and wherein the plurality of second components includes a first group of one or more second components in which the respective slot is at a first orientation relative to the respective recess, and a second group of one or more second components in which the respective slot is at a second orientation different from the first orientation relative to the respective recess, and wherein the first key orientation is aligned with and corresponds to the first slot orientation and the second key orientation is aligned with and corresponds to the second slot orientation, such that the first group of first components is adapted to properly align with and attach to only the first group of second components, while the second group of first components is adapted to properly align with and attach to only the second group of second components.

2. The set of surgical products of claim 1 wherein the plurality of first components further includes a third group of one or more first components in which the respective key is at a third orientation different from the first and second orientations relative to the respective peg, and wherein the plurality of second components further includes a third group of one or more second components in which the respective slot is at a third orientation different from the first and second orientations relative to the respective recess and wherein the third key orientation is aligned with and corresponds to the third slot orientation such that the third group of first components is adapted to properly align with and attach to only the third group of second components.

3. The set of surgical products of claim 2 wherein the plurality of first components further includes a fourth group of one or more first components in which the respective key is at a fourth orientation different from the first, second, and third orientations relative to the respective peg, and wherein the plurality of second components further includes a fourth group of one or more second components in which the respective slot is at a fourth orientation different from the first, second, and third orientations relative to the respective recess and wherein the fourth key orientation is aligned with and corresponds to the fourth slot orientation such that the fourth group of first components is adapted to properly align with and attach to only the fourth group of second components.

4. The set of surgical products of claim 1 wherein the shape of each peg and the shape of each recess are substantially cylindrical, and wherein the first and second key orientations are angularly offset relative to each other with respect to the respective substantially cylindrical peg and the first and second slot orientations are angularly offset relative to each other with respect to the respective substantially cylindrical recess.

5. The set of surgical products of claim 1 wherein the cross-sectional shape of each peg and of each recess are substantially rectangular, and wherein the first and second key orientations are offset relative to each other with respect to the respective peg and the first and second slot orientations are offset relative to each other with respect to the respective recess.

6. The set of surgical products of claim 1 wherein each of the plurality of second components includes a raised spline spaced from the corresponding respective recess and each of the plurality of first components includes an opening for fitting about one of the respective splines when in proper mating engagement therewith.

7. The set of surgical products of claim 1 wherein each key protrudes from an outer sidewall of each respective peg, and wherein each slot is located in an inner sidewall of each respective recess, and wherein the first and second key orientations are angularly offset relative to each other about the outer sidewall of each respective peg and the first and second slot orientations are angularly offset relative to each other about the inner sidewall of each respective recess.

8. The set of surgical products of claim 1 wherein each peg extends from a first noncylindrical surface and wherein each recess extends into a second mating, corresponding noncylindrical surface.

9. A set of surgical products including a plurality of first components and a plurality of second components wherein one of the first components and one of the second components are selected for engagement with each other and wherein the first components each have a key extending therefrom and wherein the second components each have a slot for corresponding engagement with one of the keys, and wherein the plurality of first components includes a first group of one or more first components in which the respective key is at a first orientation in relation to the respective first component and a second group of one or more first components in which the respective key is at a second orientation different from the first orientation in relation to the respective first component, and wherein the plurality of second components includes a first group of one or more second components in which the respective slot is at a first orientation in relation to the respective second component, and a second group of one or more second components in which the respective slot is at a second orientation different from the first orientation in relation to the respective second component, and wherein the first key orientation is aligned with and corresponds to the first slot orientation and the second key orientation is aligned with and corresponds to the second slot orientation, such that the first group of first components is adapted to properly align with and attach to only the first group of second components, while the second group of first components is adapted to properly align with and attach to only the second group of second components.

10. A set of surgical products including a plurality of provisional components and a plurality of rasp components, distinct from the provisional components, wherein one of the provisional components and one of the rasp components are selected for engagement with each other and wherein the provisional components each have a key extending therefrom and wherein the rasp components each have a slot for corresponding engagement with one of the keys and wherein the relative orientation of the respective key relative to each respective provisional component is not the same on all provisional components, and wherein the relative orientation of the respective slot relative to each respective rasp components is not the same on all rasp components, and wherein only provisional components having a key orientation that is similar to and aligns with the slot orientation of a rasp component, will properly align and mate together.

11. A set of surgical products including a plurality of provisional components and a plurality of rasp components, distinct from the provisional components, wherein one of the provisional components and one of the rasp components are selected for engagement with each other and wherein the provisional and rasp components have an attachment mechanism therebetween which includes an indexing means so that provisional components with a first indexing orientation will properly align with and attach to only rasp components with a like first indexing orientation and so that provisional components with a second indexing orientation will properly align with and attach to only rasp components with a like second indexing orientation and such that the first and second indexing orientations are different from each other and such that provisional components and rasp components having different indexing orientations will not properly align with each other for proper mating engagement.

12. A set of surgical products including a plurality of provisional components and a plurality of rasp components, distinct from the provisional components, wherein one of the provisional components and one of the rasp components are selected for engagement with each other and wherein the provisional components each have a male peg extending therefrom with a key protruding from each respective peg and wherein the rasp components each have a female recess with a slot in each respective recess for corresponding engagement with one of the keyed pegs, and wherein the plurality of provisional components includes a first group of one or more provisional components in which the respective key is at a first orientation relative to the respective peg and a second group of one or more provisional components in which the respective key is at a second orientation different from the first orientation relative to the respective peg, and wherein the plurality of rasp components includes a first group of one or more rasp components in which the respective slot is at a first orientation relative to the respective recess, and a second group of one or more rasp components in which the respective slot is at a second orientation different from the first orientation relative to the respective recess, and wherein the first key orientation is aligned with and corresponds to the first slot orientation and the second key orientation is aligned with and corresponds to the second slot orientation, such that the first group of provisional components is adapted to properly align with and attach to only the first group of rasp components, while the second group of provisional components is adapted to properly align with and attach to only the second group of rasp components.

13. The set of surgical products of claim 12 wherein the plurality of provisional components further includes a third group of one or more provisional components in which the respective key is at a third orientation different from the first and second orientations relative to the respective peg, and wherein the plurality of rasp components further includes a third group of one or more rasp components in which the respective slot is at a third orientation different from the first and second orientations relative to the respective recess and wherein the third key orientation is aligned with and corresponds to the third slot orientation such that the third group of provisional components is adapted to properly align with and attach to only the third group of rasp components.

14. The set of surgical products of claim 13 wherein the plurality of provisional components further includes a fourth group of one or more provisional components in which the respective key is at a fourth orientation different from the first, second, and third orientations relative to the respective peg, and wherein the plurality of rasp components further includes a fourth group of one or more rasp components in which the respective slot is at a fourth orientation different from the first, second, and third orientations relative to the respective recess and wherein the fourth key orientation is aligned with and corresponds to the fourth slot orientation such that the fourth group of provisional components is adapted to properly align with and attach to only the fourth group of rasp components.

15. The set of surgical products of claim 12 wherein the shape of each peg and the shape of each recess are substantially cylindrical, and wherein the first and second key orientations are angularly offset relative to each other with respect to the respective substantially cylindrical peg and the first and second slot orientations are angularly offset relative to each other with respect to the respective substantially cylindrical recess.

16. The set of surgical products of claim 12 wherein the cross-sectional shape of each peg and of each recess are substantially rectangular, and wherein the first and second key orientations are offset relative to each other with respect to the respective peg and the first and second slot orientations are offset relative to each other with respect to the respective recess.

17. The set of surgical products of claim 12 wherein each of the plurality of rasp components includes a raised spline spaced from the corresponding respective recess and each of the plurality of provisional components includes an opening for fitting about one of the respective splines when in proper mating engagement therewith.

18. A set of surgical products including a plurality of provisional components and a plurality of rasps components, distinct from the provisional components, wherein one of the provisional components and one of the rasp components are selected for engagement with each other and wherein the provisional components each have a key extending therefrom and wherein the rasp components each have a slot for corresponding engagement with one of the keys, and wherein the plurality of provisional components includes a first group of one or more provisional components in which the respective key is at a first orientation in relation to the respective provisional component and a second group of one or more provisional components in which the respective key is at a second orientation different from the first orientation in relation to the respective provisional component, and wherein the plurality of rasp components includes a first group of one or more rasp components in which the respective slot is at a first orientation in relation to the respective rasp component, and a second group of one or more rasp components in which the respective slot is at a second orientation different from the first orientation in relation to the respective rasp component, and wherein the first key orientation is aligned with and corresponds to the first slot orientation and the second key orientation is aligned with and corresponds to the second slot orientation, such that the first group of provisional components is adapted to properly align with and attach to only the first group of rasp components, while the second group of provisional components is adapted to properly align with and attach to only the second group of rasp components.

* * * * *